(12) United States Patent
Kennedy et al.

(10) Patent No.: US 10,981,116 B2
(45) Date of Patent: Apr. 20, 2021

(54) PROCESS AND SYSTEM FOR TREATING WASTE WATER AND GENERATING POWER

(71) Applicant: EnrgiStream Pty Ltd, Melbourne (AU)

(72) Inventors: Rowan John Kennedy, Melbourne (AU); James John Tanner, Melbourne (AU); Rhys Lathlain Eddy, Melbourne (AU)

(73) Assignee: EnrgiStream Pty Etd, Melbourne (AU)

( * ) Notice: Subject to any disclaimer, the term of this patent is extended or adjusted under 35 U.S.C. 154(b) by 0 days.

(21) Appl. No.: 16/083,137

(22) PCT Filed: Mar. 8, 2017

(86) PCT No.: PCT/AU2017/050202
§ 371 (c)(1),
(2) Date: Sep. 7, 2018

(87) PCT Pub. No.: WO2017/152226
PCT Pub. Date: Sep. 14, 2017

(65) Prior Publication Data
US 2019/0070560 A1    Mar. 7, 2019

(30) Foreign Application Priority Data
Mar. 9, 2016   (AU) ................................ 2016900878

(51) Int. Cl.
*B01D 61/06*    (2006.01)
*C02F 1/44*    (2006.01)
(Continued)

(52) U.S. Cl.
CPC ........... *B01D 61/06* (2013.01); *B01D 61/002* (2013.01); *B01D 61/025* (2013.01); *B01D 61/58* (2013.01); *C02F 1/441* (2013.01); *C02F 1/445* (2013.01); *C12M 21/04* (2013.01); *C12M 43/08* (2013.01); *B01D 2311/08* (2013.01); *B01D 2311/25* (2013.01); *B01D 2311/2688* (2013.01); *B01D 2313/246* (2013.01); *B01D 2313/36* (2013.01);
(Continued)

(58) Field of Classification Search
None
See application file for complete search history.

(56) References Cited

U.S. PATENT DOCUMENTS 3,220,945 A * 11/1965 Torpey ...................... C02F 3/28
    210/609
7,303,674 B2    12/2007 Lampi et al.
(Continued)

FOREIGN PATENT DOCUMENTS

JP    2014061487 A  *  4/2014
WO   2012102677 A1    8/2012

OTHER PUBLICATIONS

May 31, 2017—International Search Report and Written Opinion of International Patent Application No. PCT/AU2017/050202.

*Primary Examiner* — Krishnan S Menon
*Assistant Examiner* — Brad Gordon
(74) *Attorney, Agent, or Firm* — Banner & Witcoff, Ltd.

(57) ABSTRACT

A process for treating waste water, including the steps of extracting by forward osmosis treated water from a wastewater feed stream and transferring it to a saline draw stream, and extracting from the saline draw stream treated water by a reverse osmosis process.

5 Claims, 2 Drawing Sheets

(51) Int. Cl.
*B01D 61/00* (2006.01)
*B01D 61/02* (2006.01)
*B01D 61/58* (2006.01)
*F03G 7/00* (2006.01)
*C02F 11/04* (2006.01)
*C02F 103/00* (2006.01)
*C02F 103/08* (2006.01)
*C12M 1/107* (2006.01)
*C12M 1/00* (2006.01)
*C02F 103/06* (2006.01)

(52) U.S. Cl.
CPC ......... *C02F 11/04* (2013.01); *C02F 2103/007* (2013.01); *C02F 2103/06* (2013.01); *C02F 2103/08* (2013.01); *C02F 2303/10* (2013.01); *C02F 2303/24* (2013.01); *F03G 7/005* (2013.01); *Y02W 10/33* (2015.05); *Y02W 10/37* (2015.05)

(56) References Cited

U.S. PATENT DOCUMENTS

| | | | |
|---|---|---|---|
| 2003/0038078 A1* | 2/2003 | Stamper | C05F 17/40 210/603 |
| 2006/0144789 A1* | 7/2006 | Cath | B01D 61/58 210/641 |
| 2010/0192575 A1* | 8/2010 | Al-Mayahi | F01K 25/06 60/671 |
| 2014/0224718 A1* | 8/2014 | Hancock | B01D 65/02 210/195.2 |
| 2014/0238938 A1* | 8/2014 | Sarp | C02F 1/445 210/641 |
| 2015/0352497 A1* | 12/2015 | Sakai | C02F 1/441 210/252 |
| 2016/0002073 A1 | 1/2016 | Nowosielski-Slepowron | |
| 2016/0002074 A1* | 1/2016 | Benton | B01D 61/02 210/636 |
| 2016/0038880 A1* | 2/2016 | Benton | B01D 61/027 210/641 |

* cited by examiner

PROCESS AND SYSTEM FOR TREATING WASTE WATER AND GENERATING POWER

CROSS-REFERENCE TO RELATED APPLICATIONS

This application is a U.S. National Stage application under 35 U.S.C. § 371 of international Application PCT/AU2017/50202 filed Mar. 8, 2017, which claims the benefit of priority to Application AU 2016900878, filed Mar. 9, 2016. Benefit of the filing date of each of these prior applications is hereby claimed. Each of these prior applications is hereby incorporated by reference in their entirety.

FIELD OF THE INVENTION

The present invention relates to a process and system for treating waste water. The present invention also relates to generating electrical power from such a process. More particularly but not exclusively, the present invention relates to the treatment of sewerage.

BACKGROUND OF THE INVENTION

The treatment of wastewater from cities and towns presents ongoing problems for engineers. The basic objective of protection of public health must now be met with treatment processes that have minimal impact on the environment. Traditional treatment processes, such as an activated sludge plant, require large amounts of energy. Plant operators have increasingly been implementing biogas systems to offset their energy use.

Osmosis has previously been used in the filtration of water. Osmosis is the naturally occurring movement of solvent through a semi-permeable membrane from an area of low solute concentration to an area of higher concentration. The movement of solvent tends to equalise the concentration on both sides of the membrane creating a pressure differential ($\Delta P$) over the membrane. The osmotic pressure, $\Delta Po$, is the pressure differential when the solvent is in equilibrium and there is no net flow through the membrane. The osmotic pressure varies for different solvents and solute concentrations.

Osmotic power, by way of a pressure retarded osmosis (PRO) system, has previously been proposed for power generation as osmotic power is a renewable resource that is currently untapped and has the potential to become a significant source of reliable power.

Previously proposed PRO systems have required a source of fresh water, along with a source of salinated water, for operation, resulting in limited potential sites for their use.

Furthermore, such an approach ignores the potential of waste water sources, such as waste water for example, for use in PRO systems.

Examples of the invention seek to solve, or at least ameliorate, one or more disadvantages of previous wastewater treatment and pressure retarded osmosis systems.

SUMMARY OF THE INVENTION

According to one aspect of the present invention, there is provided a process for treating waste water, including the steps of extracting by forward osmosis treated water from a wastewater feed stream and transferring it to a saline draw stream, and extracting from the saline draw stream treated water by a reverse osmosis process.

According to another aspect of the present invention, there is provided a process for treating waste water, including the steps of extracting by forward osmosis treated water from a wastewater feed stream and transferring it to a saline draw stream drawn from a natural source of salinated water.

According to another aspect of the present invention, there is provided a process for treating waste water, including the step of passing a waste water feed stream and a saline draw stream through a forward osmosis apparatus to extract treated water from the waste water and dilute the saline draw stream, wherein the saline draw stream is provided via a saline draw stream circuit to the forward osmosis apparatus and the treated water is extracted from the diluted saline draw stream downstream of the forward osmosis apparatus by a reverse osmosis process.

According to a preferred embodiment, hydraulic energy generated in the saline draw stream from the forward osmosis process is used by the reverse osmosis process. The saline draw stream circuit may be a closed loop circuit.

According to another aspect of the present invention, there is provided a process for treating waste water, including the step of passing a waste water feed stream and a saline draw stream through a forward osmosis apparatus to extract clean water from the waste water, wherein the saline draw stream is drawn from a natural source of salinated water.

The natural source of salinated water may be an ocean, sea, river, bore, inlet or ground water and the saline draw solution is returned to the natural source of salinated water as diluted salinated water after passing through the forward osmosis module, thereby discharging a portion of the waste water.

Preferably, the saline draw solution is discharged to the natural source of salinated water via a diffuser for dispersing the saline draw solution.

The process may further include the step of extracting hydraulic energy from the saline draw solution after the forward osmosis process. The energy extracted is preferably used in a reverse osmosis process for extracting treated water from the diluted saline draw solution.

The process may further include the step of providing concentrated waste water exiting the forward osmosis module to a biogas reactor for the production of electricity. Preferably, the biogas reactor incorporates an anaerobic digestion process. The process may include the step of extracting inert solids from the biogas reactor.

Preferably, process includes the step of filtering the waste water prior to introduction into the forward osmosis module to remove particulates and/or grit.

Preferably, the wastewater is sewerage.

According to another aspect of the present invention, there is provided a system for treating waste water, comprising:
  a waste water feed line for introducing waste water;
  a saline draw solution circuit for introducing saline draw solution;
  a forward osmosis apparatus in communication with the waste water feed line and the saline draw solution circuit for extracting treated water from the waste water feed line and transferring it into the saline draw solution circuit to dilute the saline draw solution; and
  a reverse osmosis apparatus in the saline draw solution circuit for extracting treated water from the diluted saline draw stream and for re-supplying undiluted saline draw solution to the forward osmosis module for extracting further treated water from the waste water feed line.

The saline draw solution circuit may be a closed loop circuit.

According to another aspect of the present invention, there is provided a system for treating waste water, comprising:
- a waste water feed line for introducing waste water;
- a saline draw solution feed line for introducing saline draw solution from a natural source of salinated water; and
- a forward osmosis apparatus in communication with the waste water feed line and the saline draw solution feed line for extracting treated water from the waste water feed line and transferring it into the saline draw solution to dilute the saline draw solution;
- a discharge line for discharging the diluted saline draw solution to the natural source of salinated water.

Preferably, the system is configured for treating sewerage supplied via the waste water feed line.

BRIEF DESCRIPTION OF THE DRAWINGS

Preferred embodiments of the invention will be further described, by way of non-limiting example only, with reference to the accompanying drawings in which.

DETAILED DESCRIPTION

Figure 1:
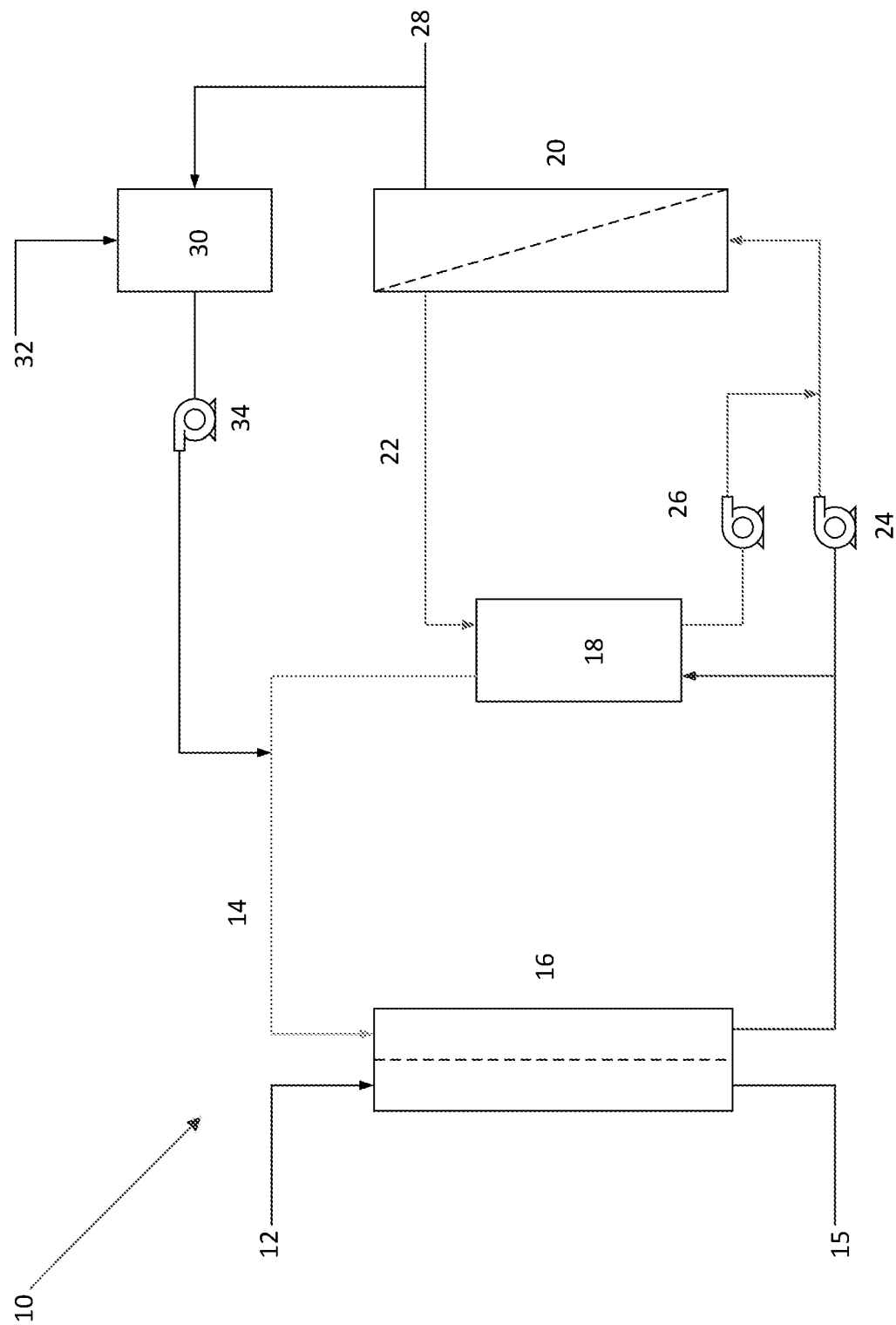
FIG. 1 is a schematic diagram of a process for treating waste water of one embodiment of the invention.

With reference to FIG. 1, there is shown schematically a system 10 for treating waste water according to a preferred embodiment of the present invention.

The system 10 includes a waste water feed line 12 for introducing waste water, a saline draw solution circuit 14 for introducing saline draw solution, a forward osmosis apparatus in the form of module 16 which is in communication with the waste water feed line 12 and the saline draw solution circuit 14 for extracting treated water from the waste water feed line 12 and transferring it into the saline draw solution circuit 14 to dilute the saline draw solution, and a reverse osmosis apparatus in the form of module 20 which is in communication with the saline draw solution circuit 14 for extracting treated water from the diluted saline draw solution so that undiluted saline draw solution can be re-supplied to the forward osmosis module 16 for extracting further treated water from the waste water in the feed line 12.

In preferred embodiments, the waste water fed to the system 10 via the feed line 12 is sewerage, though in other embodiments the waste water may be stormwater runoff or runoff from combined stormwater/sewer systems, or other forms of waste water.

The illustrated embodiment includes a pressure exchanger 18 in the saline draw solution circuit 14 and a reverse osmosis circuit 22 for providing pressure from the saline draw solution circuit 14 to the reverse osmosis circuit 22 to at least partially power the reverse osmosis module 16. In other embodiments, the reverse osmosis module 16 may be powered by other means, such as via a separate power supply for example.

In use of the system 10 the waste water feed line 12 and the saline draw solution circuit 14 allow passage through opposites sides of the forward osmosis module 16, whereby treated water passes through a semi-permeable membrane to extract treated water from the waste water in the feed line 12 and dilute the saline draw solution.

Concentrated waste water exits the forward osmosis module 16 via conduit 15 for further treatment, as will be discussed further below. Diluted saline draw solution also exits the forward osmosis module 16 before being communicated to reverse osmosis module 20 where treated water is extracted from the saline draw solution, thereby providing clean, potable water.

Hydraulic energy generated in the saline draw solution circuit 14 from the forward osmosis process is used in the reverse osmosis circuit 22 to assist with pumping the diluted saline draw solution through the reverse osmosis module 20. To achieve this, pressure exchanger 18 is provided in the saline draw solution circuit 14 to transfer energy to the reverse osmosis circuit 22. It will be appreciated that additional power will be required to drive the reverse osmosis process. It will also be appreciated that pressure exchanger 18 may take make many different forms, such as a rotary pressure exchanger, or be operable by various other means, such as pistons for example.

In the illustrated embodiment, only a portion of the diluted saline draw solution passes from the saline draw solution circuit 14 to the reverse osmosis circuit 22. A high pressure pump 24 may be provided to provide high pressure saline draw solution to the reverse osmosis module 20. A recirculation pump 26 may also be provided for circulating water from the pressure exchanger 18 to the reverse osmosis module 20.

Treated water may exit the reverse osmosis module 20 through treated water discharge 28 for use as clean potable water. A portion of the treated water may be used to top-up the saline draw solution to account for system losses. In this regard, treated water is fed into a brine tank 30 for mixing with salt introduced via inlet 32, which is pumped via makeup pump 34 back into the saline draw solution circuit 14.

In preferred embodiments, the saline draw solution circuit 14 is generally a closed loop circuit.

Figure 2:
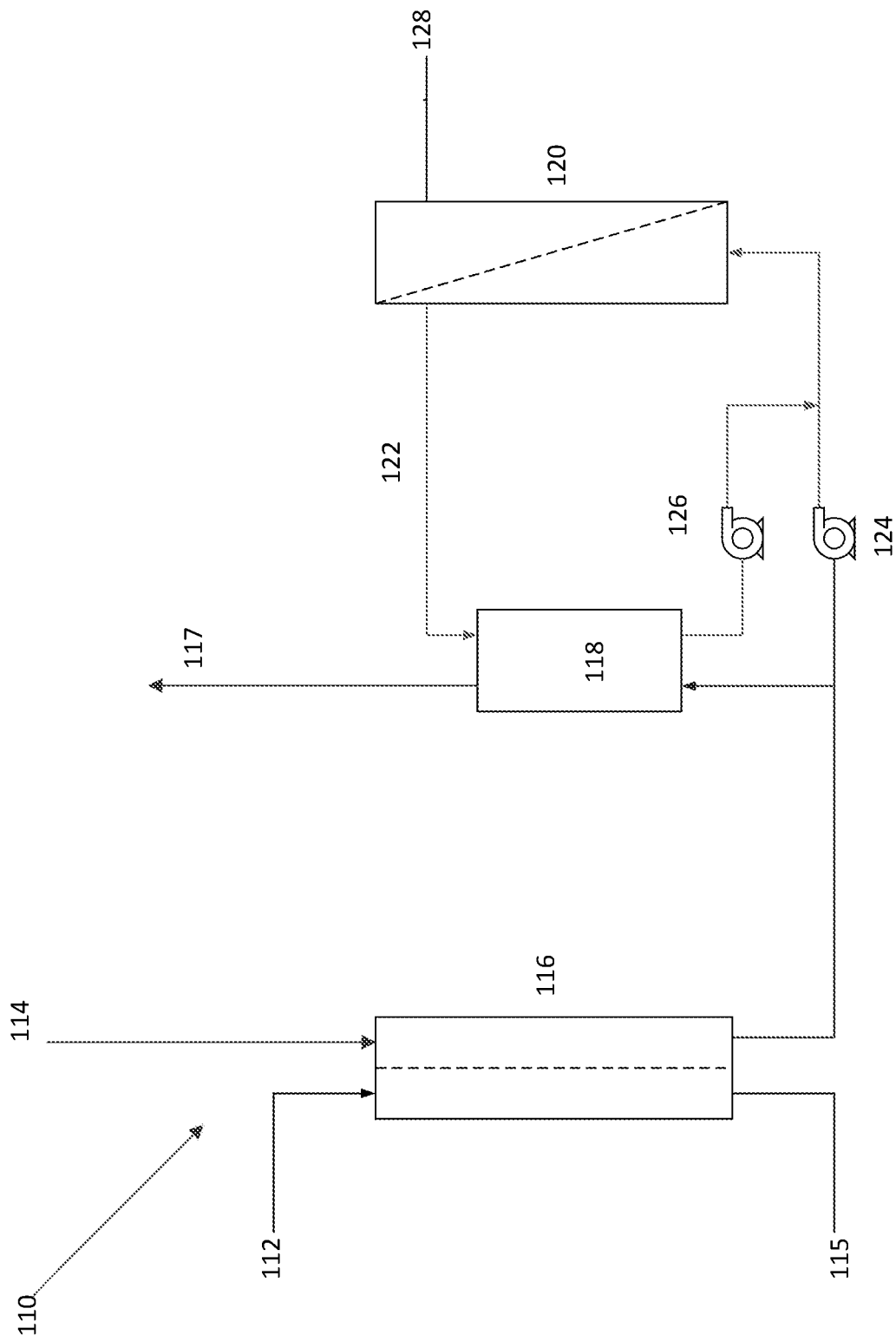
FIG. 2 is a schematic diagram of a process for treating waste water of another embodiment of the invention.

With reference to FIG. 2, there is shown a system 100 for treating waste water according to another embodiment of the present invention. System 100 includes many components common to system 10 and like components have been given like reference numerals incremented by 100.

The system 100 includes a waste water feed line 112 for introducing waste water, a saline draw solution feed line 114 for introducing saline draw solution from a natural source of salinated water, a forward osmosis apparatus in the form of module 116 in communication with the waste water feed line 112 and the saline draw solution feed line 114 for extracting treated water from the waste water feed line 112 and transferring it into the saline draw solution to dilute the saline draw solution, and a discharge line 117 for discharging the diluted saline draw solution to the natural source of salinated water.

In a preferred embodiment, the system 110 is configured for treating sewerage supplied via the waste water feed line 112.

In use of system 110, a waste water feed stream and a saline draw solution are passed, via respective waste water feed line 112 and a saline draw solution feed line 114, through opposites sides of a forward osmosis module 116 to extract clean water from the waste water and transfer it to the saline draw solution to dilute the saline draw solution.

The saline draw solution feed line 114 is drawn from a natural source of salinated water, which may be any naturally occurring source of salinated water such as for example an ocean, sea, river, inlet, bore or ground water. Alternatively, the source of salinated water may be man made, such as a salt lake for example, or from industrial process waste.

Following passing through the forward osmosis module 116, the saline draw solution is returned to the natural source of salinated water as diluted salinated water, thereby safely discharging a portion of the waste water which may previously have been discharged directly into the natural source of salinated water. By mixing salinated water with treated water in the forward osmosis member 16, 116, the treated water discharged to the natural source of salinated water has a higher salt content, thereby minimising environmental impacts. Preferably, the saline draw solution is discharged to the natural source of salinated water via a diffuser (not shown).

System 110 also includes means 118 for extracting hydraulic energy from the saline draw solution after the forward osmosis process. In one example, said means 118 includes a water turbine, such as a Pelton wheel or a Francis turbine, for generating electricity. In another example, said means 118 includes a pressure exchanger for providing pressure to a reverse osmosis circuit 122 for partially powering a reverse osmosis module 120 for extracting treated water from the diluted saline draw solution, thereby providing clean, potable water as a process output via treated water outlet 128.

System 110 may also include a high pressure pump 124 to provide high pressure saline draw solution to the reverse osmosis module 120. A recirculation pump 126 may also be provided for circulating water from the means 118 to the reverse osmosis module 120.

Either system 10 or system 110 may include a number of optional features, such as a storage tank prior to the forward osmosis module 16, 116 to balance flow of the waste water into the forward osmosis module 16, 116. Also, a biogas reactor (not shown) may be provided for receiving concentrated waste water exiting the forward osmosis module 16, 116 for the production of electricity. It is expected that the forward osmosis module 16 will remove 80% to 90% of the water from the waste water stream, thereby providing a thick sludge for use in the biogas reactor. In a preferred form, the biogas reactor incorporates an anaerobic digestion process.

By utilising a biogas reactor, the treatment process may be completely powered, a reverse osmosis module potentially powered to supply clean potable water, and any excess energy returned to the grid and exported for sale. It is expected that generating electricity from the described and illustrated systems will be cheaper than the long term average cost of solar and wind power. Accordingly, the described systems may be very beneficial to coastal communities.

Following processing through the biogas reactor, inert solids may be extracted and sold for agricultural use as bio-solids produced by a biogas production process typically contain higher levels of nutrients such as nitrates, phosphates and potassium (than are present in conventional sewage sludge)—these nutrients being amenable to extraction or those nutrients can remain in the bio solids and can be used as a land application fertiliser.

Biogas production and electricity generation is typically not affected by the use of the present systems because it uses a fundamentally different source of energy. In fact, biogas production may be more efficient due to the higher concentration of carbon and nitrogen in the feedstock for methane producing microorganisms. Smaller feed volumes also require less heat to reach optimum conditions and smaller vessels could be used with lower costs. Furthermore, consistent gas generation and cheap balancing storage could provide base load power that would complement load following power supplied by the forward osmosis process.

Previous renewal power generation systems have difficultly accounting for variations in electricity demand. In the present systems, the volume of wastewater that enters a plant varies according to a diurnal pattern and therefore the potential amount of energy that can be generated is expected to also be subject to this pattern. The demand for energy and the wholesale price also varies according to a diurnal pattern which has been observed to be similar in shape to that of wastewater flows. This is logical as the consumption of energy and generation of wastewater are both driven by the level of human activity, thereby allowing power generated by the present systems to be better matched with demand.

This is a significant benefit over other renewable technologies such as solar and wind energy, where the generation patterns are unpredictable and of variable output. Matching the pattern of generation and consumption leads to an efficient system. In addition, the potential energy of untreated waste water can be stored cheaply for short periods of time by adding storage upstream of the membrane. This would allow some control to smooth the peaks and adjust generation capacity to meet demand. Again, this is an advantage over other types of generation that require energy to be stored in expensive batteries.

Furthermore, either system preferably includes a filter or primary treatment system for pre-filtering the waste water prior to introduction into the forward osmosis module 16, 116 to remove particulates and/or grit and prevent fouling of the forward osmosis module 16, 116.

The described and illustrated systems and processes preferably make use of wastewater in the form of sewerage, which is available at any habitable site and previously required energy for disposal. Advantageously, the described and illustrated systems and processes can treat sewerage without drawing external energy, potentially cheaper than existing sewerage treatment options, provide clean potable water, and potentially return electrical power into an energy grid. Furthermore, the described and illustrated systems and processes can be utilised at sites that are either coastal or remote therefrom. In this regard, system 10, which utilises a generally closed loop saline draw solution, is presented as being more suitable for treating wastewater at locations remote from a coast and system 110 is presented as being more suitable for treating wastewater at coastal locations where a source of salinated water is readily available.

Where wastewater is treated but the process does not include the production of potable water by desalination, it is expected that the process will always produce surplus electricity for export. Where the wastewater is treated and the process includes the production of potable water by desalination, energy savings in the order of 30% to 50% are expected when compared to a reverse osmosis process alone. Furthermore, where the wastewater is treated and the process includes the production of potable water by desalination, the process will start to produce surplus electricity for export when the concentration of COD (chemical oxygen demand) in the wastewater exceeds 2000 mg per litre. COD is a measure of the organic waste content in the water. By way of example, the COD concentration in typical sewage from Australian capital cities is 600. The COD in the sewage and wastewater stream for a regional Australian centre which has a significant abattoir, dairy or food processing industry will be in in the range of 2000-3000. COD concentration in sewage and wastewater streams in Asian cities and towns will be in the range of 2000-3000 mg/l.

Using a biogas reactor in combination with the forward osmosis filtration system for treating sewerage is particularly effective as extracting water from the sewerage concentrates the sewerage, thereby increasing the COD to higher levels to enable efficient anaerobic digestion to occur. In contrast, directly using anaerobic digestion in connection with municipal waste water can be generally inefficient due to relatively low COD concentrations.

Preferred embodiments of the present invention use previously untapped osmotic power, by way of a pressure retarded osmosis (PRO) system, to treat wastewater and generate energy. The process also provides excellent water treatment performance and could be easily retrofitted into existing waste water treatment plants. The described and illustrated process uses a much smaller footprint than conventional activated sludge treatment (CAS) and other wastewater treatment processes as there are no settling ponds or aeration tanks, allowing the process to be undertaken in a small factory.

Forward osmosis membranes operate in the same manner as reverse osmosis membranes and therefore the rejection rates for pollutants are expected to be very similar and it is expected that that the forward osmosis membrane will be able to reject greater than 98% of dissolved solids, bacteria, pathogens and virus, minerals and nutrients, toxic heavy metals and BOD. This treated water is expected to be comparable with tertiary level treated water (excluding salts) and would be suitable for direct environmental discharge.

The embodiments have been described by way of example only and modifications are possible within the scope of the invention disclosed. For example, although the processes and systems described herein have been described in relation to sewerage treatment, treatment of other wastewater streams, such as industrial waste water, mining waste water, combined storm water and sewer waste water, ship board waste water, and landfill leachate treatment.

The invention claimed is:

1. A process for treating waste water, including the steps of:
    extracting, by a forward osmosis module, treated water from a wastewater feed stream and transferring the treated water to a saline draw stream located in a saline draw solution circuit, the saline draw solution circuit being coupled to a pressure exchanger;
    passing the saline draw stream to a reverse osmosis module located in a reverse osmosis circuit, the reverse osmosis circuit being coupled to the pressure exchanger,
    extracting the treated water from the saline draw stream via the reverse osmosis module;
    providing concentrated waste water exiting the forward osmosis module to a biogas reactor for production of electricity, wherein the biogas reactor incorporates an anaerobic digestion process; and
    extracting inert solids from the biogas reactor,
    wherein the pressure exchanger provides pressure from the saline draw solution circuit to the reverse osmosis circuit to at least partially power the reverse osmosis module;
    wherein at least a portion of the treated water extracted via the reverse osmosis module is used to generate additional saline draw solution; and
    the generated saline draw solution is added to the saline draw solution circuit.

2. A process according to claim 1, wherein the saline draw stream is drawn from a natural source of salinated water.

3. A process according to claim 1, further including the step of filtering the wastewater feed stream prior to introduction into the forward osmosis module to remove particulates and/or grit.

4. A process according to claim 1, wherein the wastewater feed stream comprises sewerage.

5. A process for treating waste water, including a step of passing a waste water feed stream and a saline draw stream through a forward osmosis module to extract potable water from the waste water, wherein the saline draw stream is drawn from a natural source of salinated water;
    wherein the saline draw stream is coupled to a pressure exchanger;
    passing the saline draw stream to a reverse osmosis module located in a reverse osmosis circuit, the reverse osmosis circuit being coupled to the pressure exchanger,
    extracting treated water from the saline draw stream via the reverse osmosis module;
    providing concentrated waste water exiting the forward osmosis module to a biogas reactor for production of electricity, wherein the biogas reactor incorporates an anaerobic digestion process; and
    extracting inert solids from the biogas reactor;
    wherein the pressure exchanger provides pressure from the saline draw stream to the reverse osmosis circuit to at least partially power the reverse osmosis module;
    wherein at least a portion of the treated water extracted via the reverse osmosis module is used to generate additional saline draw solution; and
    the generated saline draw solution is added to a saline draw solution circuit.

* * * * *